(12) United States Patent
Biggs

(10) Patent No.: US 12,303,395 B2
(45) Date of Patent: May 20, 2025

(54) HIP IMPLANT

(71) Applicant: XERXES ARTHROPEDIX LLC, Naples, FL (US)

(72) Inventor: Henry Kurtis Biggs, Naples, FL (US)

(73) Assignee: XERXES ARTHROPEDIX LLC, Naples, FL (US)

( * ) Notice: Subject to any disclaimer, the term of this patent is extended or adjusted under 35 U.S.C. 154(b) by 897 days.

(21) Appl. No.: 17/091,699

(22) Filed: Nov. 6, 2020

(65) Prior Publication Data
US 2021/0137688 A1 May 13, 2021

Related U.S. Application Data

(60) Provisional application No. 62/943,100, filed on Dec. 3, 2019, provisional application No. 62/939,111, filed on Nov. 22, 2019, provisional application No. 62/931,856, filed on Nov. 7, 2019.

(51) Int. Cl.
*A61F 2/36* (2006.01)
*A61F 2/30* (2006.01)

(52) U.S. Cl.
CPC ... *A61F 2/3662* (2013.01); *A61F 2002/30112* (2013.01); *A61F 2002/30332* (2013.01); *A61F 2002/3625* (2013.01); *A61F 2002/3686* (2013.01); *A61F 2310/00407* (2013.01); *A61F 2310/00796* (2013.01)

(58) Field of Classification Search
CPC ............ A61F 2/3662; A61F 2002/3678; A61F 2002/3686; A61F 2002/3698; A61F 2002/2825; A61F 2/32; A61F 2/36
See application file for complete search history.

(56) References Cited

U.S. PATENT DOCUMENTS

| | | | |
|---|---|---|---|
| 3,781,917 A * | 1/1974 | Mathys | A61F 2/36 606/65 |
| 4,435,854 A | 3/1984 | Keller | |
| 4,589,883 A | 5/1986 | Kenna | |

(Continued)

FOREIGN PATENT DOCUMENTS

| | | | | |
|---|---|---|---|---|
| CN | 1416330 A | * | 5/2003 | ......... A61F 2/30767 |
| CN | 111297519 B | | 5/2021 | |

(Continued)

OTHER PUBLICATIONS

Notice of Rejection, issued in corresponding Japanese Application No. 2022-525620, dated Jul. 12, 2024, 18 pages (with English Translation).

*Primary Examiner* — Christopher D. Prone
(74) *Attorney, Agent, or Firm* — Cozen O'Connor

(57) ABSTRACT

A hip implant for use in hip replacement surgical procedures. The hip implant comprises a femoral stem body designed for fixation in two planes, i.e. the AP plane and the lateral plane. The curvature of the implant is designed to mirror the geometry of the femur, thus providing for more contact points with the inner surface of the medullary cavity. The outer surface curvature cooperates with the inner surface associated with the medullary cavity. The hip implant is designed to provide increased or maximum contact with the interior of the bone, i.e. femur, while decreasing or minimizing stress risers or stress points, thus reducing the likelihood of patient pain and/or implant failure.

21 Claims, 19 Drawing Sheets

(56) References Cited

U.S. PATENT DOCUMENTS

| | | | |
|---|---|---|---|
| 4,704,686 A * | 11/1987 | Aldinger | A61F 2/3662 |
| | | | 623/914 |
| 4,738,681 A | 4/1988 | Koeneman et al. | |
| 4,871,369 A | 10/1989 | Muller | |
| 8,936,649 B2 | 1/2015 | Huff | |
| 2005/0055103 A1 | 3/2005 | Badatcheff et al. | |
| 2008/0234833 A1 * | 9/2008 | Bandoh | A61F 2/30942 |
| | | | 623/18.11 |
| 2010/0286792 A1 | 11/2010 | Wang et al. | |
| 2018/0318093 A1 | 11/2018 | Kirwan | |
| 2019/0038421 A1 | 2/2019 | Wang et al. | |
| 2023/0009989 A1 | 1/2023 | De Villiers et al. | |

FOREIGN PATENT DOCUMENTS

| | | | | |
|---|---|---|---|---|
| EP | 0390883 | | 10/1990 | |
| EP | 0617933 | | 10/1994 | |
| EP | 0808618 | | 11/1997 | |
| FR | 264012 | * | 10/1990 | A61F 2/36 |
| FR | 2662932 | | 12/1991 | |
| FR | 2676914 | | 12/1992 | |
| GB | 2318296 A | | 4/1998 | |
| JP | 0641963 | | 3/1985 | |
| JP | 1993137739 | | 6/1993 | |
| JP | 2001037792 A | | 2/2001 | |

* cited by examiner

| CONFIGURATION NAME | | DEFAULT | LARGER | SMALLER |
|---|---|---|---|---|
| AP CURVE ⌵ | D3 | 5.00mm | 5.00mm | 4.67mm |
| | D4 | 75.00mm | 75.00mm | 70.06mm |
| | D5 | 91.00mm | 91.00mm | 85.00mm |
| | D7 | 11.50mm | 11.50mm | 10.74mm |
| | D8 | 11.75mm | 11.75mm | 10.98mm |
| LATERAL CURVE ⌵ | D2 | 6.00mm | 6.00mm | 5.60mm |
| | D5 | 12.50mm | 12.50mm | 11.68mm |
| | D6 | 16.47mm | 16.47mm | 15.38mm |
| PT2 ⌵ | D1 | 10.00mm | 10.44mm | 9.34mm |
| PT3 ⌵ | D1 | 40.00mm | 41.76mm | 37.36mm |
| PT4 ⌵ | D1 | 80.00mm | 83.52mm | 74.73mm |

HIP IMPLANT

CROSS REFERENCE

In accordance with 37 C.F.R. 1.76, a claim of priority is included in an Application Data Sheet filed concurrently herewith. Accordingly, the present invention claims priority to U.S. Provisional Application No. 62/931,856, entitled, "HIP IMPLANT", filed Nov. 7, 2019, U.S. Provisional Application No. 62/939,111, entitled, "HIP IMPLANT", filed Nov. 22, 2019, and U.S. Provisional Application No. 62/943,100, entitled, "HIP IMPLANT", filed Dec. 3, 2019. The contents of the above referenced applications are incorporated herein by reference in their entirety.

FIELD OF THE INVENTION

The present invention relates to medical devices; to implant devices; and more particularly, to hip joint prosthesis or hip joint implants and use thereof in hip replacement procedures.

BACKGROUND OF THE INVENTION

Hip implants, or hip prosthesis, are typically used to help individuals in need restore mobility and alleviate pain related to various medical conditions, such as hip disease or injuries, or as a result of arthritis. In general, hip replacement surgery entails various anatomical structures of an individual's hip being replaced with artificial components designed to function like normal anatomical features. Typically, an artificial acetabular cup is implanted in place of the individual's acetabulum. In addition, a femoral prosthesis is implanted into the patient's femur. While many hip replacement procedures have been successfully performed, long term patient success often relies on how well the implant fits within the femur.

SUMMARY OF THE INVENTION

The present invention relates to a hip implant for use in hip replacement surgical procedures. The hip implant comprises a femoral stem body designed for fixation in two planes, i.e. the anterior-posterior (AP) plane and the lateral plane. The curvature of the implant is designed to mirror the geometry of the femur, thus providing more contact points with the inner surface of the medullary cavity. The outer surface curvature cooperates with the inner surface associated with the medullary cavity. The hip implant is designed to provide increased or maximum contact with the interior of the bone, i.e. femur, while decreasing or minimizing stress risers or stress points, thus reducing the likelihood of patient pain and/or implant failure.

Accordingly, it is an objective of the invention to provide an improved hip implant for use in hip replacement surgical procedures.

It is a further objective of the invention to provide an improved hip implant for use in hip replacement surgical procedures designed for fixation in the AP plane.

It is yet another objective of the invention to provide an improved hip implant for use in hip replacement surgical procedures designed for fixation in the lateral plane.

It is a still further objective of the invention to provide an improved hip implant for use in hip replacement surgical procedures designed for fixation in two planes, the AP plane and the lateral plane.

It is a further objective of the invention to provide an improved hip implant for use in hip replacement surgical procedures having curvature in two different planes.

It is yet another objective of the invention to provide an improved hip implant for use in hip replacement surgical procedures having curvature in the AP plane and the lateral plane.

It is a still further objective of the invention to provide an improved hip implant for use in hip replacement surgical procedures having curvature which mirrors the curvature of the inner surface of the medullary cavity.

It is a further objective of the invention to provide an improved hip implant for use in hip replacement surgical procedures configured to maintain sufficient surface contact with the inner surface of the medullary cavity to reduce stress risers.

It is yet another objective of the invention to provide an improved hip implant for use in hip replacement surgical procedures configured to more evenly distribute stress loads.

It is a still further objective of the invention to provide an improved hip implant for use in hip replacement surgical procedures configured to provide multiple contact points when inserted into a femur.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 19A is a table showing an illustrative example of tableted curve values associated with 3D curves of the spinal implant device;

DETAILED DESCRIPTION OF THE INVENTION

Figure 1:
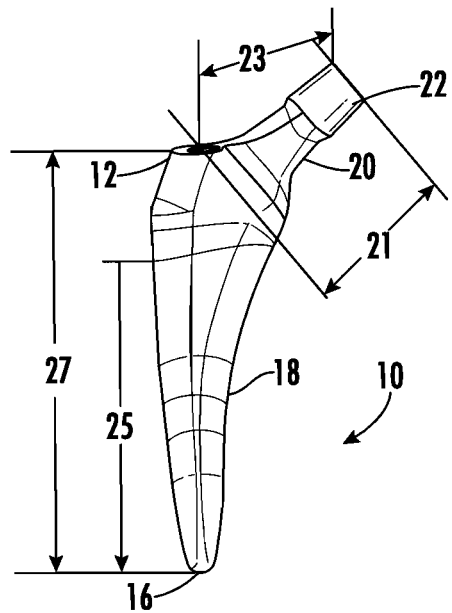
FIG. 1 is a perspective view of an illustrative embodiment of a hip implant device, shown in an AP view.
Figure 2:
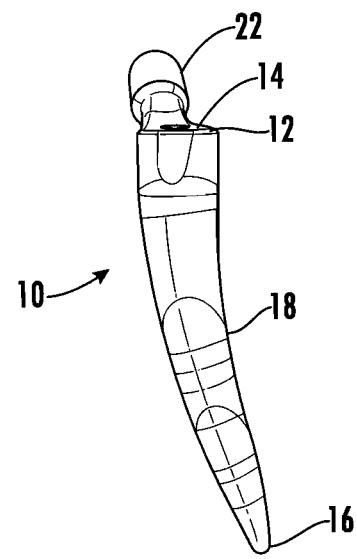
FIG. 2 is a perspective view of the hip implant device, shown in the lateral view, illustrating the back side of the hip implant device.
Figure 3:
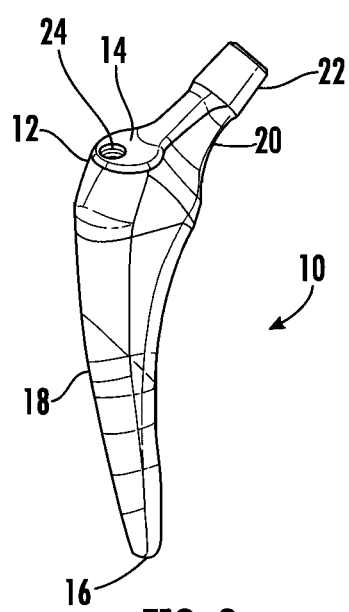
FIG. 3 is an alternative perspective view of the hip implant device.
Figure 4:
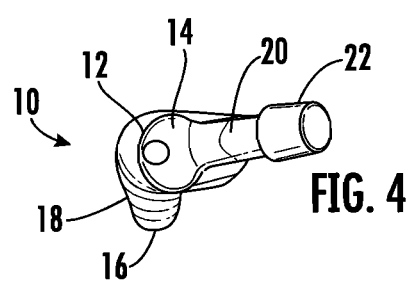
FIG. 4 is a top view of the hip implant device.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-4, an illustrative example of a hip implant device for use in hip replacement surgical procedures, referred to generally as hip implant 10, is shown. The geometrical shape and/or curvature associated with the geometrical shape of the implant 10 is designed to have the longest load bearing surface possible, or maximum contact with the bone, when inserted therein, thus decreasing stress points. The longer the bearing surface created, more than a single contact spot with the bone is provided. The hip implant 10 has a proximal end 12, with proximal surface 14, a distal tip 16, and a main body 18, also referred to as a stem 18. At the proximal end 12 is a neck portion 20. The stem 18, or the hip implant 10 overall, may be designed to have or maintain an oval shape in cross section to spread out the load. This shape provides pressure to the bone in a hoop manner. The neck portion 20 terminates in a femoral head engaging member 22, illustrated herein as a locking taper. The locking taper may be, for example, a Jarno locking taper or a Brown & Sharp locking taper. The femoral head engaging member 22 is sized and shaped to engage with an implant acetabular liner and/or an implant femoral head so as to engage with an acetabular socket. The proximal surface 14 may contain a threaded opening 24 sized and shaped to receive a securing member, such as a screw.

In an illustrative embodiment, the hip implant 10 may be designed to have a neck length 21 of 34-44 mm. The hip implant 10 may include an offset 23. The stem may further be defined by a medial stem length 25 and a lateral stem length 27. To aid in securing the hip implant 10 to the femur, a portion of the stem 18 may include a porous coating, such as a titanium plasma spray (200 mm micrometer porosity) with a hydroxyapatite coating. A separate portion of the hip implant may include a roughened section with a hydroxyapatite coating. Preferably, the hip implant 10 will allow for bone growth to a portion of thereto, preferably to the top ⅔ of the hip implant 10. The distal tip 16 is preferably designed to prevent binding to the bone when inserted therein.

The hip implant 10 is designed to optimize the proper fit when inserted into a femur, particularly mirroring the shape of the inner surface of the medullary cavity. The hip implant stem 18 is designed for fixation in two planes, i.e. the AP plane and the lateral plane. Such fixation is accomplished through curvatures of the hip implant 10 along the AP plane and the lateral plane. In addition, the outer surface curvature is designed to cooperate with the inner surface associated with the medullary cavity. The geometrical shape resulting from these curvatures allows the hip implant 10 to achieve more contact points with the inner surface of the medullary cavity.

Figure 5:
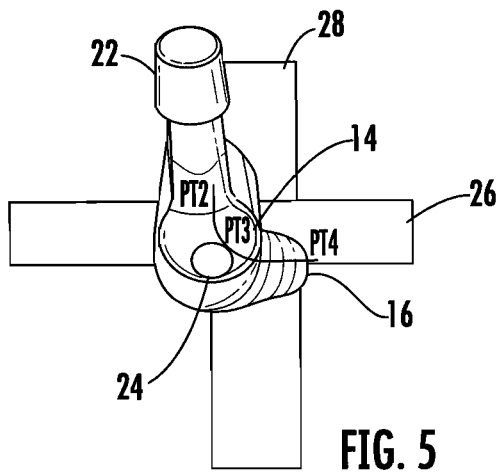
FIG. 5 is a top view of the hip implant device, illustrating the curvature of the device viewed in the AP plane and curvature of the device viewed in the lateral plane.
Figure 6:
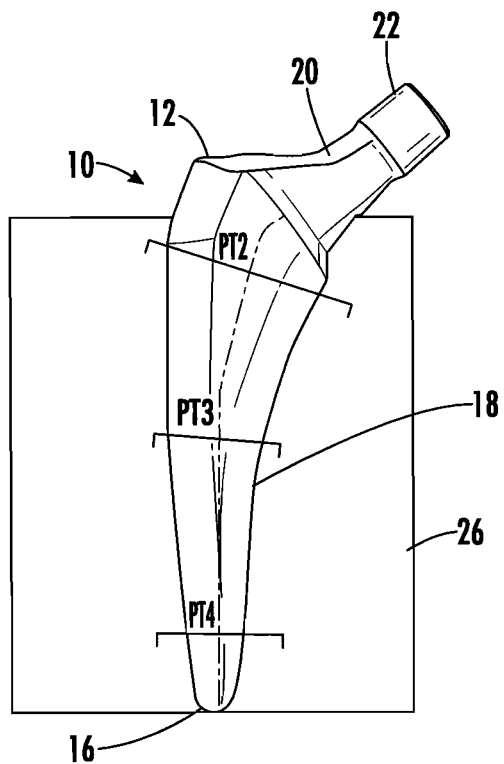
FIG. 6 illustrates the curvature of the device in the AP plane.
Figure 7:
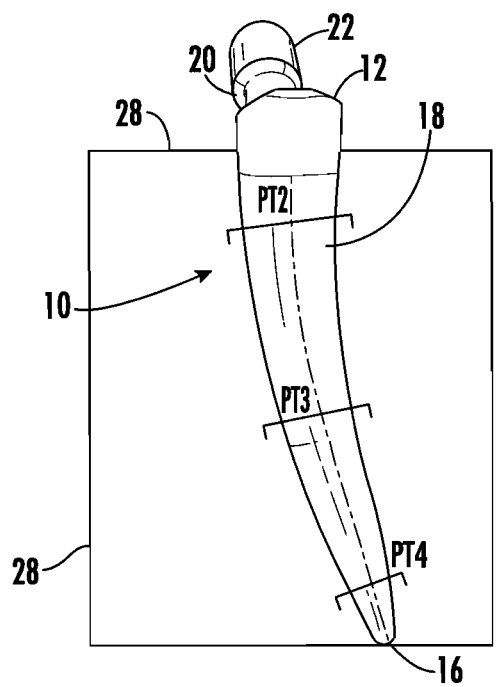
FIG. 7 illustrates the curvature of the device in the lateral plane.
Figure 8:
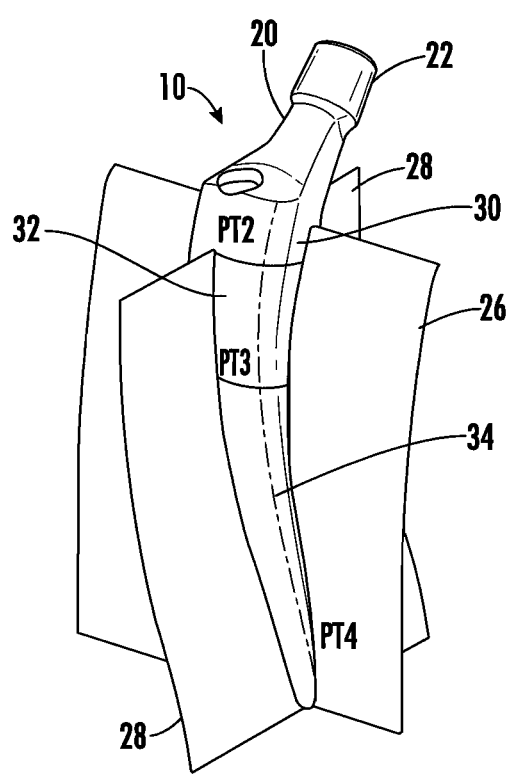
FIG. 8 illustrates the intersecting of the two curvature planes along the length of the hip implant device.
Figure 9:
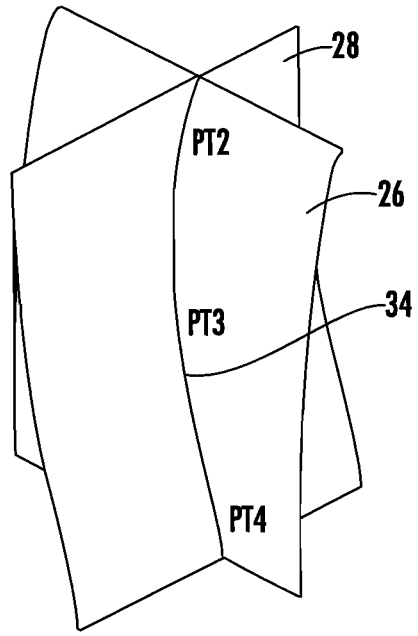
FIG. 9 illustrates the intersection of the AP plane and lateral plane along the length of the hip implant device (hip implant device removed for illustrative purposes), showing the hip implant device longitudinal axis along the length of the hip implant device.

FIG. 5 is a top view of the hip implant 10 looking down towards the distal tip 16. The figure illustrates the two planes, the AP plane 26 moving down along the length of the stem 18, and the lateral plane 28 that moves down along the length of the stem 18 and outwardly towards the viewer. FIG. 6 illustrates the hip implant 10 in the AP view, showing the AP plane 26. FIG. 7 illustrates the hip implant 10 in the lateral view, showing the lateral plane 28. FIG. 8 illustrates the intersection of the AP plane 26 and the lateral plane 28 along the length of the hip implant 10. Both planes represent the geometrical shaped curvature associated with the surfaces associated with these planes. Accordingly, surface 30 has a curvature along the length of the implant 10 shown by the AP plane 26. Surface 32 has a curvature along the length of the implant 10 shown by the lateral plane 28. A longitudinal axis (see also FIG. 9, with the hip implant 10 removed to illustrate this axis) is defined by the intersection of the two planes, AP plane 26 and lateral plane 28, along the length of the hip implant 10. From this longitudinal axis 34, the size of the hip implant device 10 can be defined as a length extending out (in all directions) from the longitudinal axis 34 to as far as required, preferably a sufficient distance so at least a portion of an outer surface of the hip implant 10 contacts an inner surface of the medullary canal.

Figure 10:
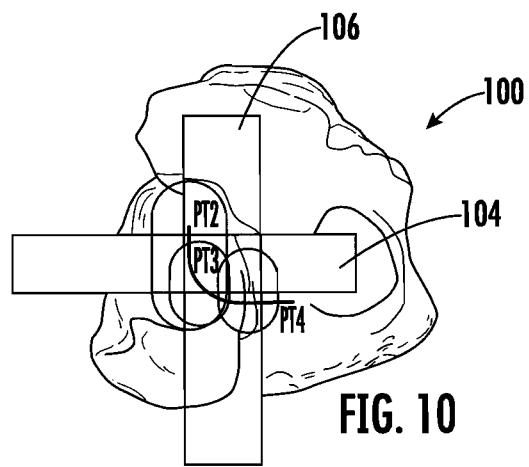
FIG. 10 is a top view of a femur, without the hip implant device inserted therein.
Figure 11:
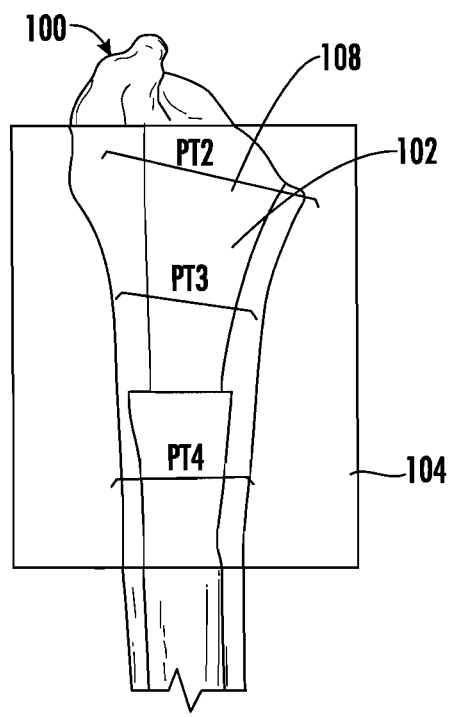
FIG. 11 is an AP view of the femur shown in FIG. 10.
Figure 12:
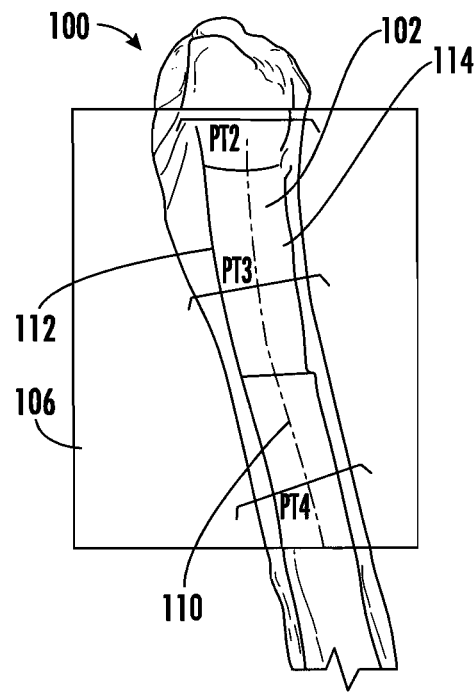
FIG. 12 is a lateral view of the femur shown in FIG. 10.
Figure 13:
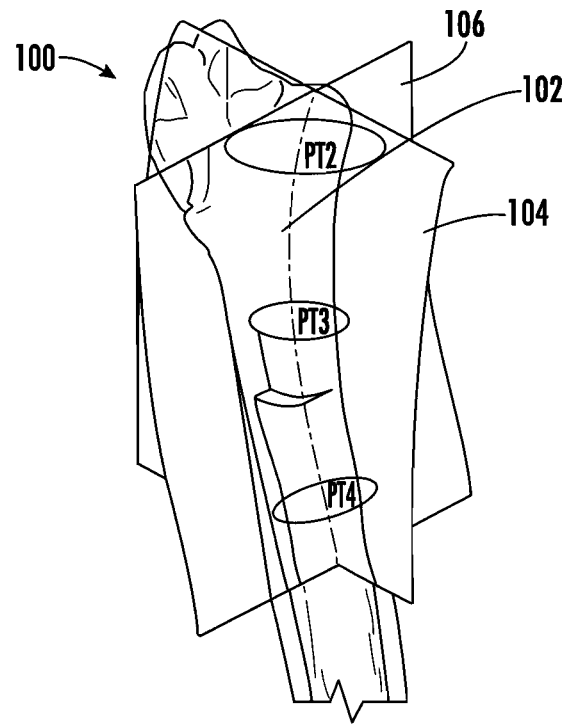
FIG. 13 illustrates an alternative view of the femur shown in FIG. 10, and the intersection of the two planes along the length of the hip implant device.
Figure 14:
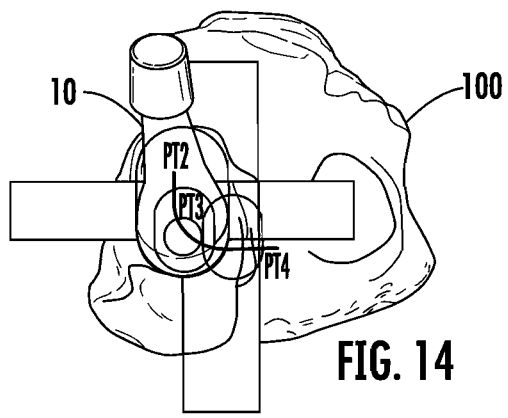
FIG. 14 is a top view of the hip implant device, shown implanted within a femur.
Figure 15:
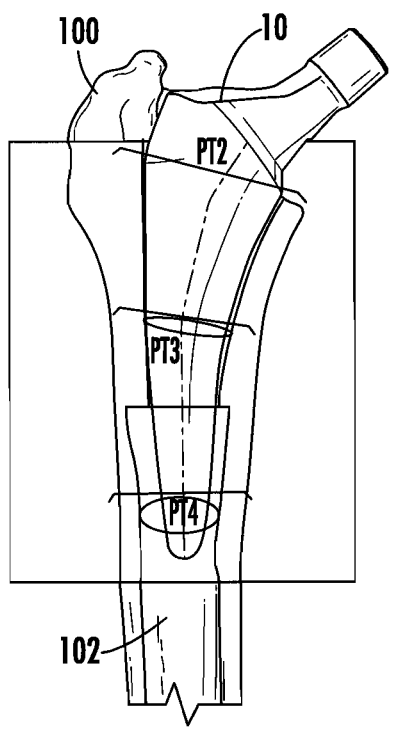
FIG. 15 illustrates an AP view of the implanted hip implant device shown in FIG. 14.
Figure 16:
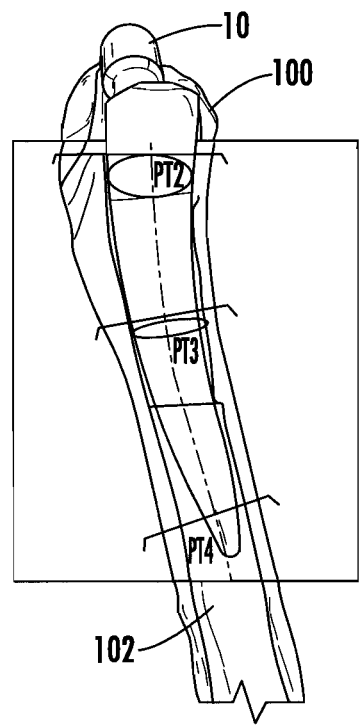
FIG. 16 illustrates a lateral view of the implanted hip implant device shown in FIG. 14.
Figure 17:
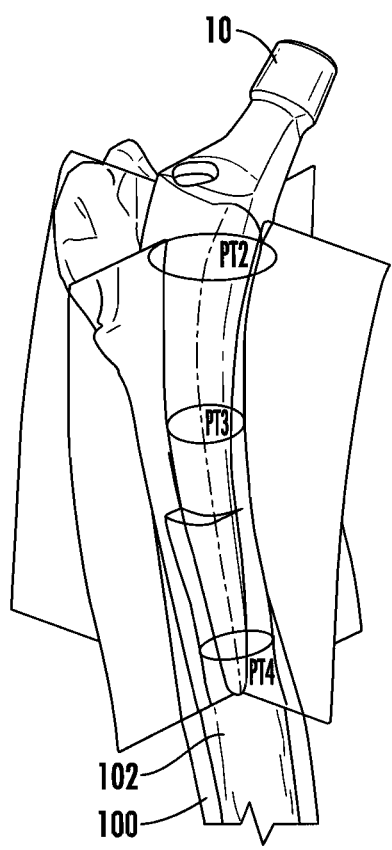
FIG. 17 is an alternative view of the implanted hip implant device shown in FIG. 14.

FIGS. 10-13 illustrate an embodiment of a femur 100, with the medullary cavity 102. FIG. 10 is a top view of the femur 100, shown with a femur AP plane 104 and femur lateral plane 106. FIG. 11 illustrates the femur AP plane 104 with femur AP view longitudinal axis 108. FIG. 12 illustrates the femur lateral plane 106, with femur lateral view longitudinal axis 110. FIG. 13 provides an alternative perspective view of the femur 100, showing the intersection of the femur AP plane 104 and the femur lateral plane 106. As the hip implant 10 is configured to mirror the anatomical features of the femur, the geometrical shape of the hip implant 10, particularly the curvatures, is designed to provide an anatomical fit in order to maximize surface contact with the inner surfaces 112, 114 of the medullary cavity 102.

Figure 18:
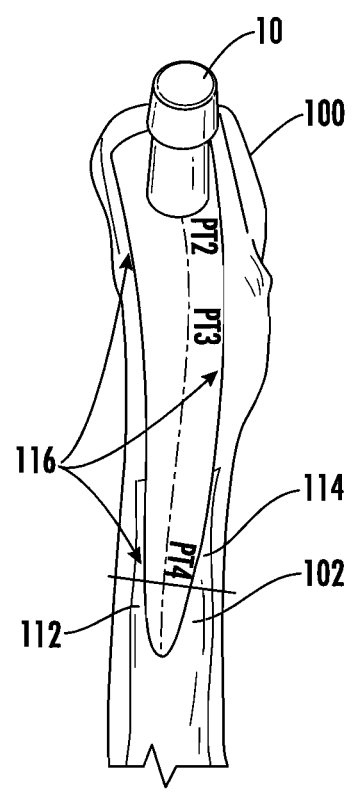
FIG. 18 shows a lateral view of the implanted hip implant device, illustrating multi-contact points with the femur.

Referring to FIGS. 14-18, the hip implant 10 is shown inserted into the femur 100, resting within the medullary cavity 102. Based on the geometrical shape and/or curvatures of the hip implant 10, when inserted into the femur, the implant device 10 makes maximum contact with the inner surfaces 112, 114 of the medullary cavity 102. Referring specifically to FIG. 18, multipoint contact points 116 are illustrated.

In a preferred embodiment, the distal tip portion 16 has a rounded or blunt shape. In addition, the distal tip 16 may also have a secondary curvature, preferably curving back towards the center. This secondary curvature, as well as the blunt tip, helps reduce the likelihood of side pain for the patient when the hip implant 10 is inserted into the medullary cavity 102. The secondary curvature should be sufficient so the distal tip 16 does not contact or run up against any portion of the femur.

Figure 19B:
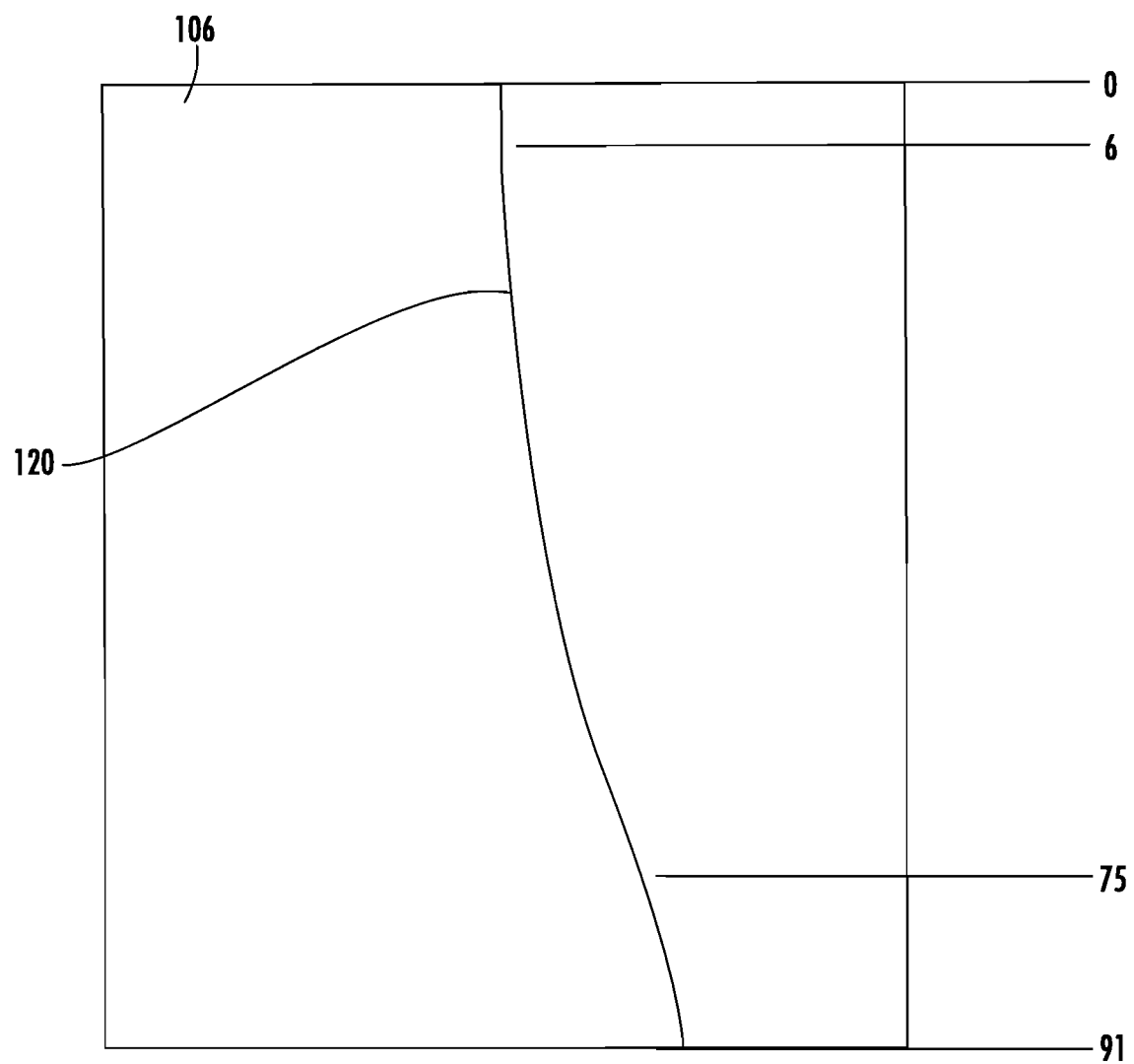
FIG. 19B is a parametrically-defined 2D curve that conforms to the general anatomical shape of the upper femur generated in the lateral view, with the curve generated from the tabulated values shown in FIG. 19A.
Figure 19C:
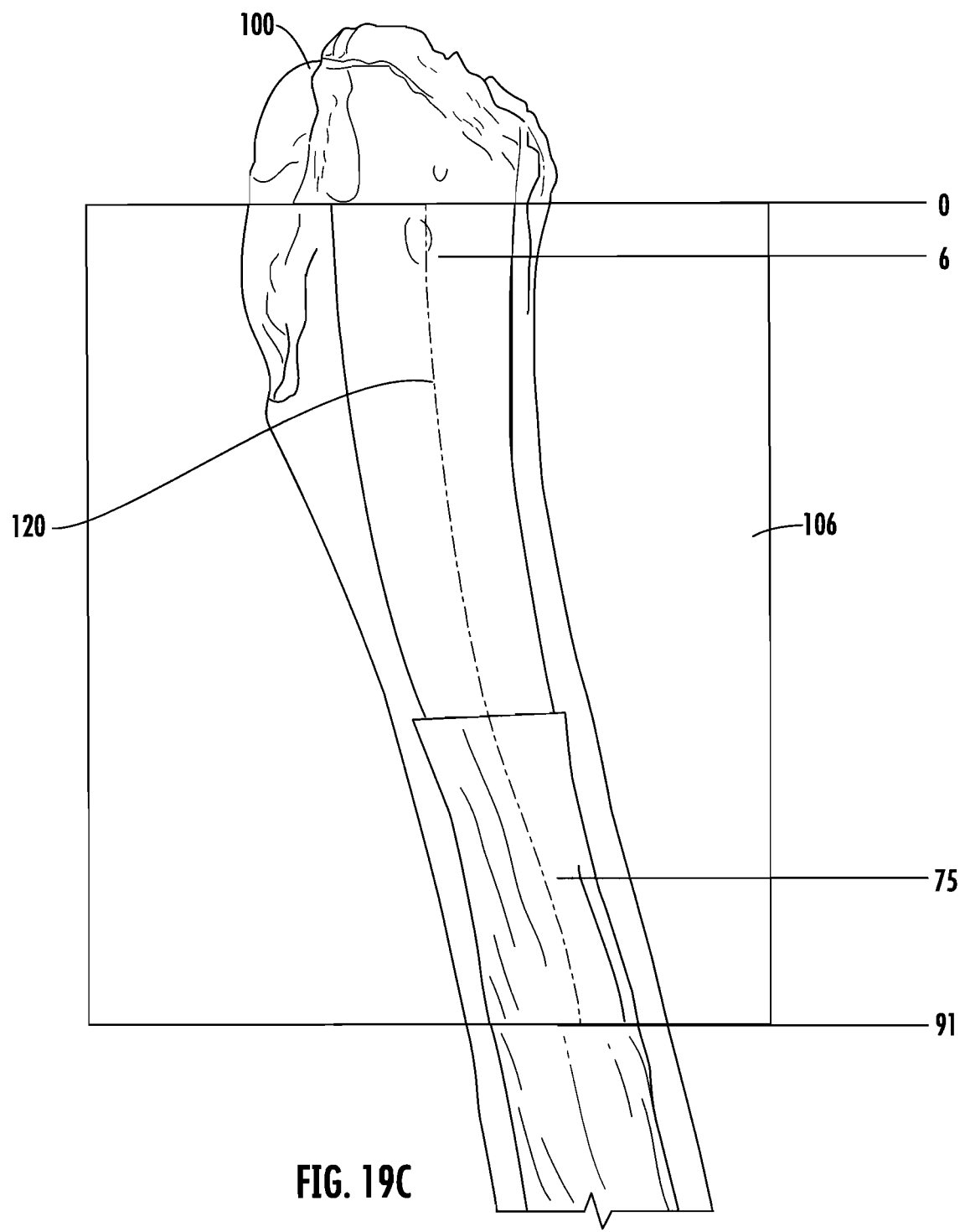
FIG. 19C illustrates the parametrically-defined 2D curve shown in FIG. 19B, overlaid with the femoral anatomy.
Figure 19D:
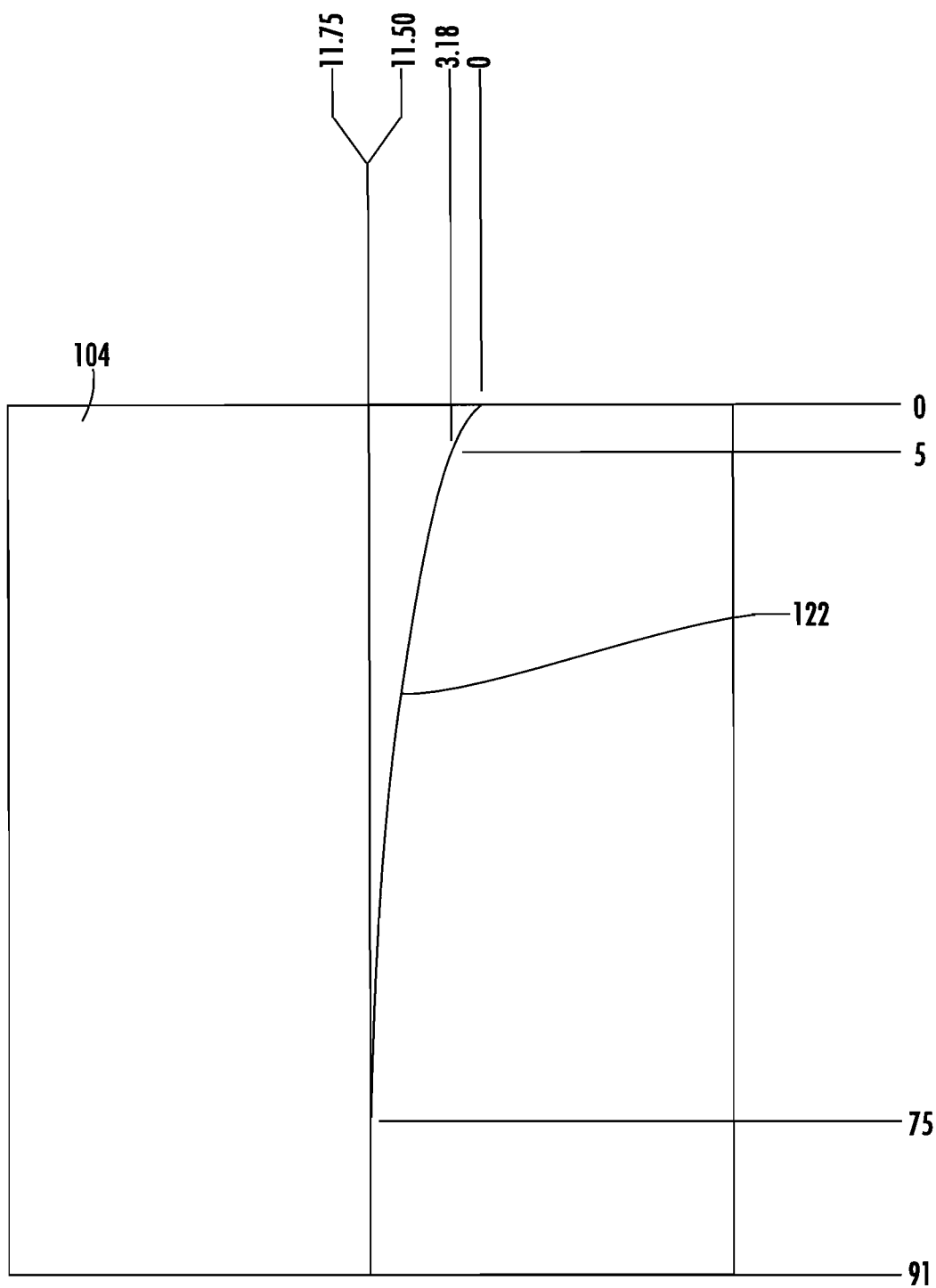
FIG. 19D is a parametrically-defined 2D curve that conforms to the general anatomical shape of the upper femur generated in the AP view, with the curve generated from the tabulated values shown in FIG. 19A.
Figure 19E:
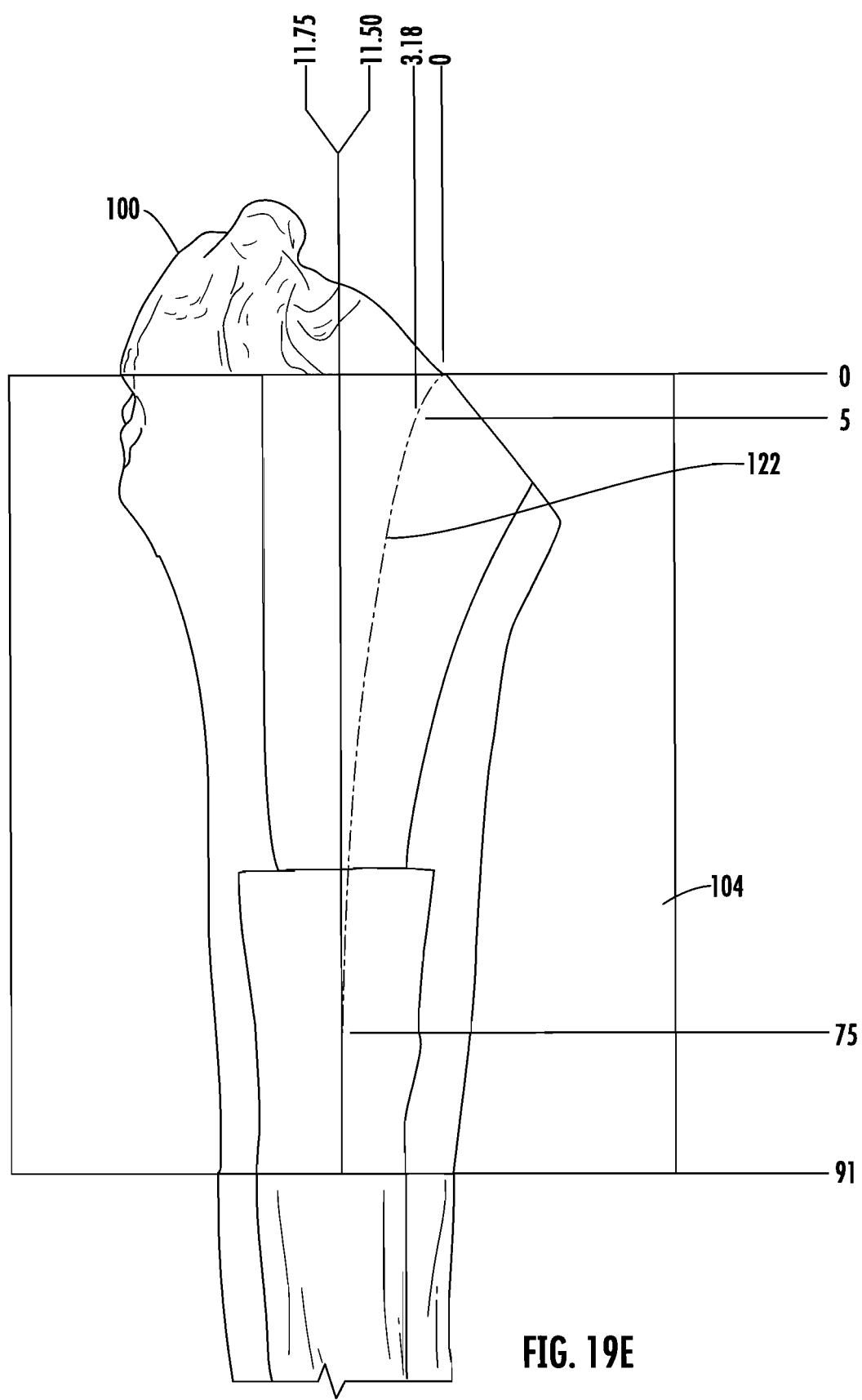
FIG. 19E illustrates the parametrically-defined 2D curve shown in FIG. 19D, overlaid with the femoral anatomy.

The geometrical shape of the hip implant 10 can be determined by tabulated reference values using characteristic three-dimensional curve. FIG. 19A illustrates table 118 representing examples of tabulated reference (curve) values. Based on the tabulated values, a parametrically-defined 2D curve that conforms to the general anatomical shape of the upper femur 100 is generated in the lateral view; see FIGS. 19B and 19C. FIG. 19B shows the hip implant stem lateral view curve 120. In FIG. 19C, the femoral anatomy 100 is shown overlaying the image shown in FIG. 19B. Based on the tabulated values, a parametrically-defined 2D curve that conforms to the general anatomical shape of the upper femur 100 can also be generated in the anterior-posterior (AP) view, see FIGS. 19D and 19E. FIG. 19D shows the hip implant stem AP view curve 122. In FIG. 19E, the femoral anatomy 100 is shown overlaying the image shown in FIG. 19D.

Figure 20A:
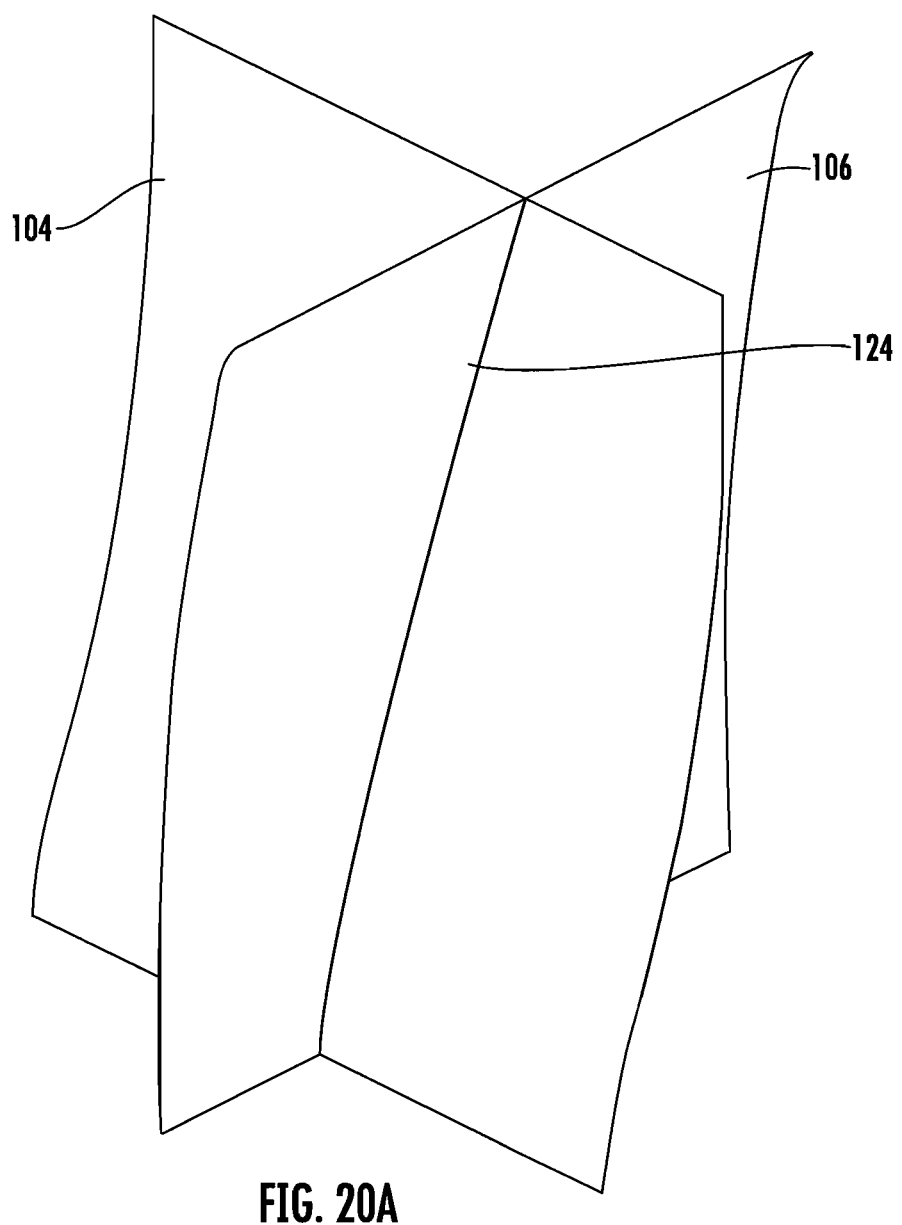
FIG. 20A is a characteristic 3D curve of the hip implant device, defined as the intersection of surfaces created by linearly translating both 2D curves shown in FIG. 19B and FIG. 19D perpendicularly to their respective views.
Figure 20B:
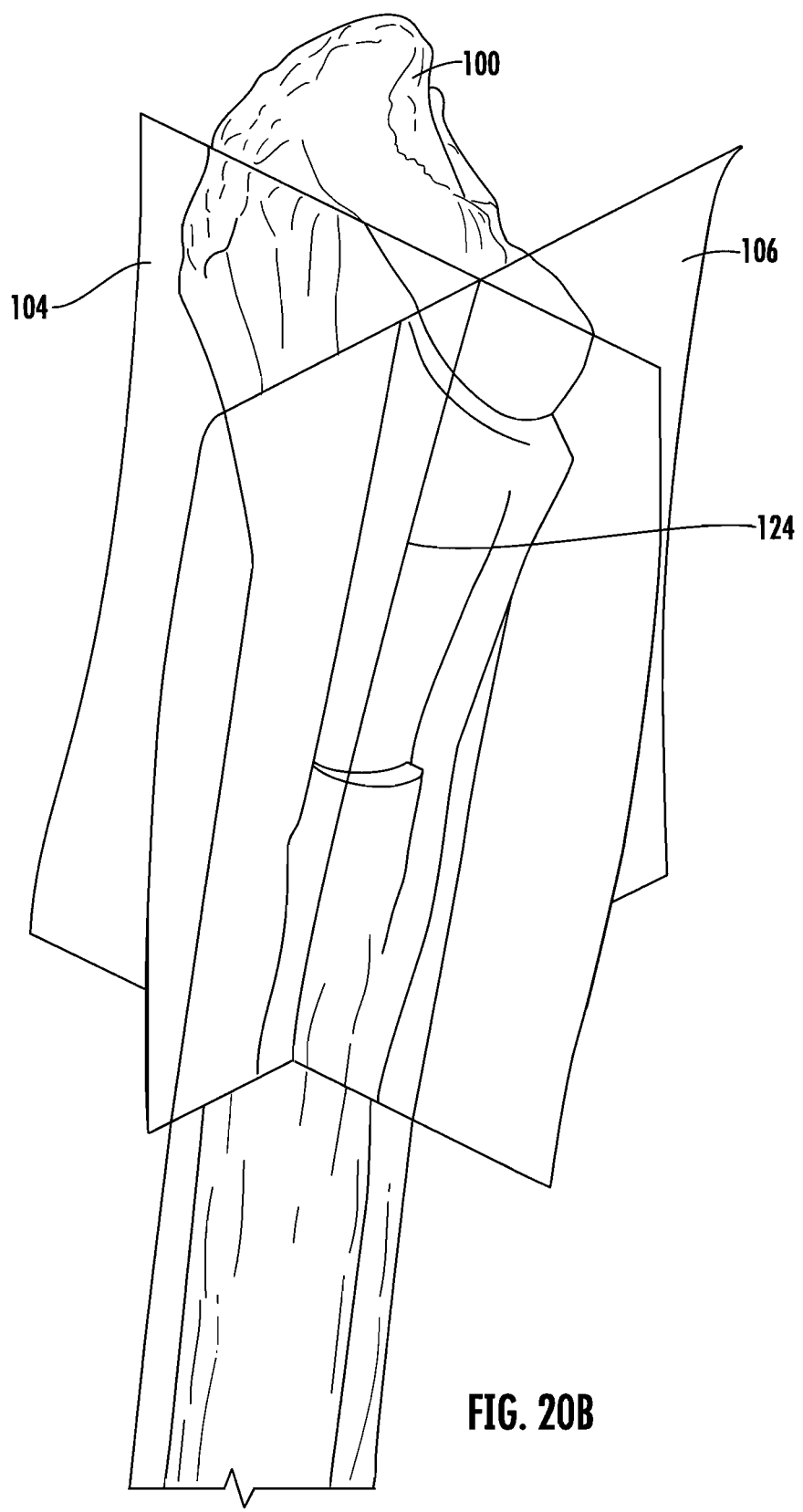
FIG. 20B illustrates the 3D curve of the hip implant device shown in FIG. 20A, overlaid with the femoral anatomy.
Figure 21A:
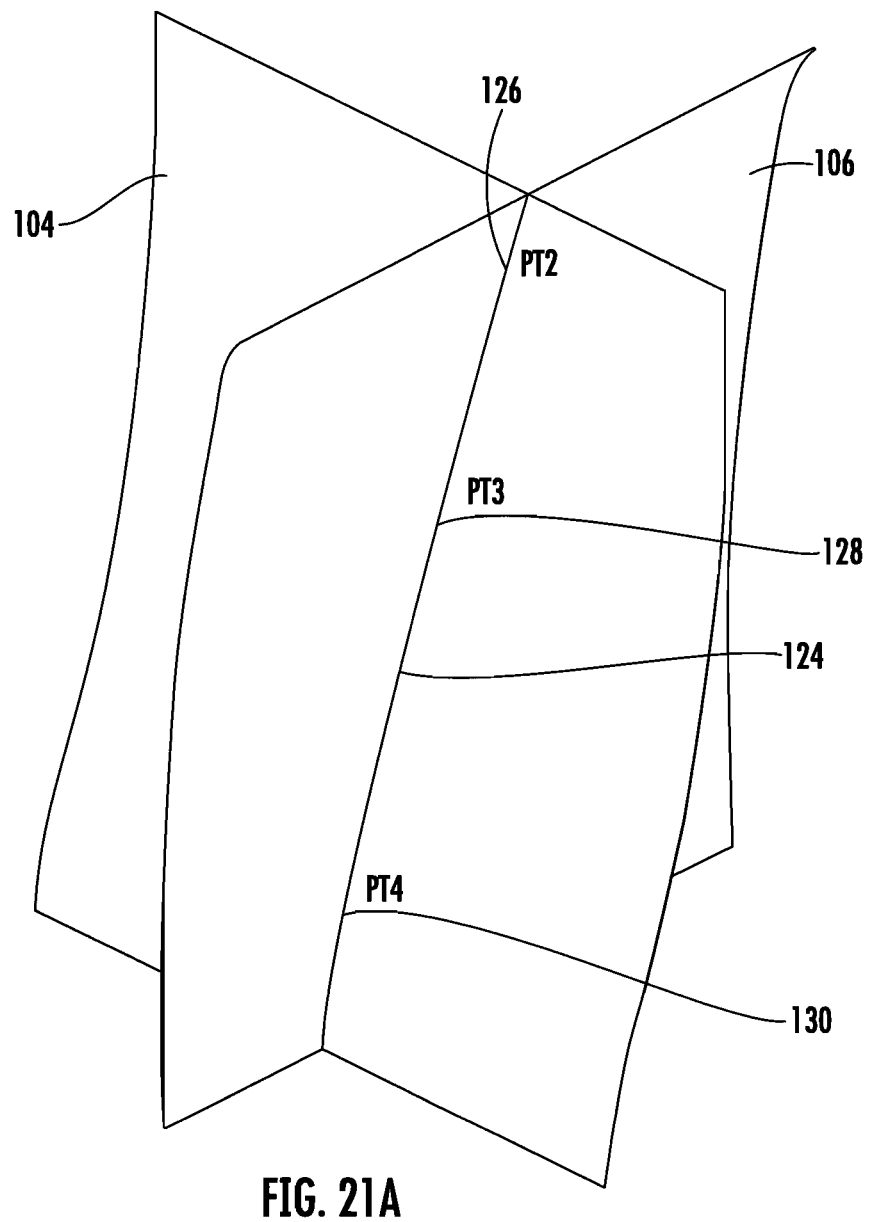
FIG. 21A illustrates intermediate reference points shown on the resultant 3D curve of the hip implant device and positioned by tabulated parametric arc-length dimensions relative to one end.
Figure 21B:
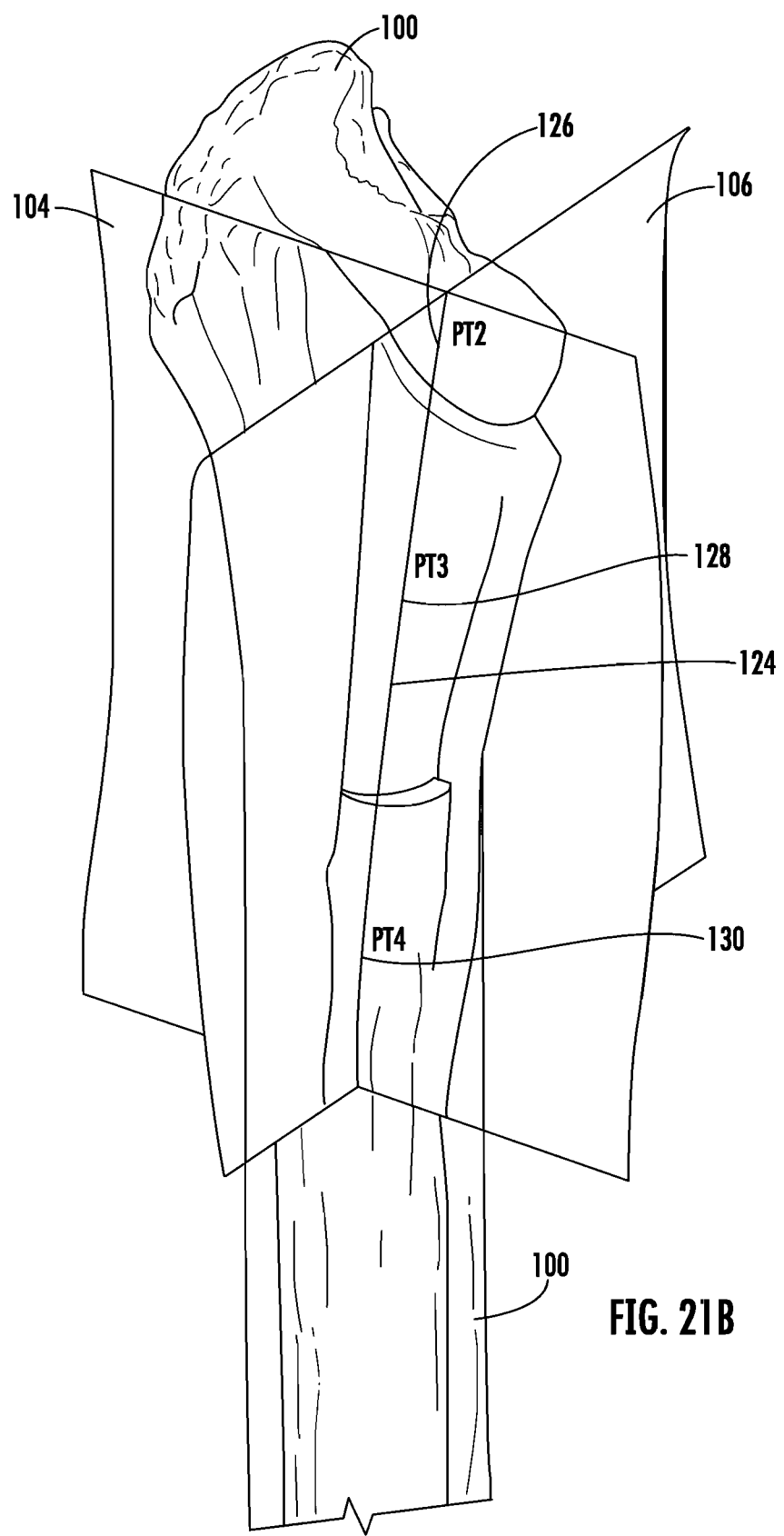
FIG. 21B illustrates the intermediate reference points shown in FIG. 21A in context with the femoral anatomy.
Figure 22A:
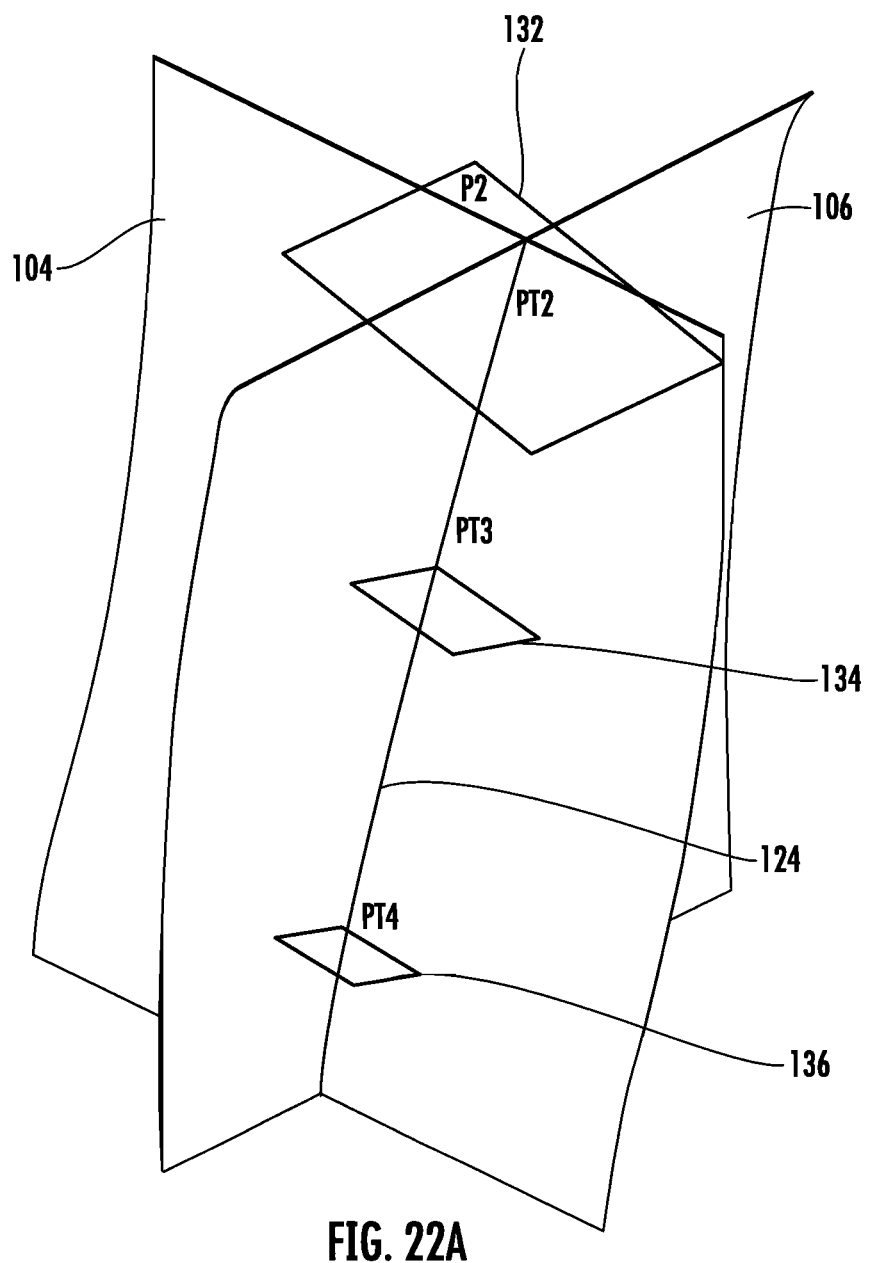
FIG. 22A illustrates normal cross section planes located at each of the reference points illustrated in FIG. 21A or FIG. 21B of the 3D curve of the hip implant.
Figure 22B:
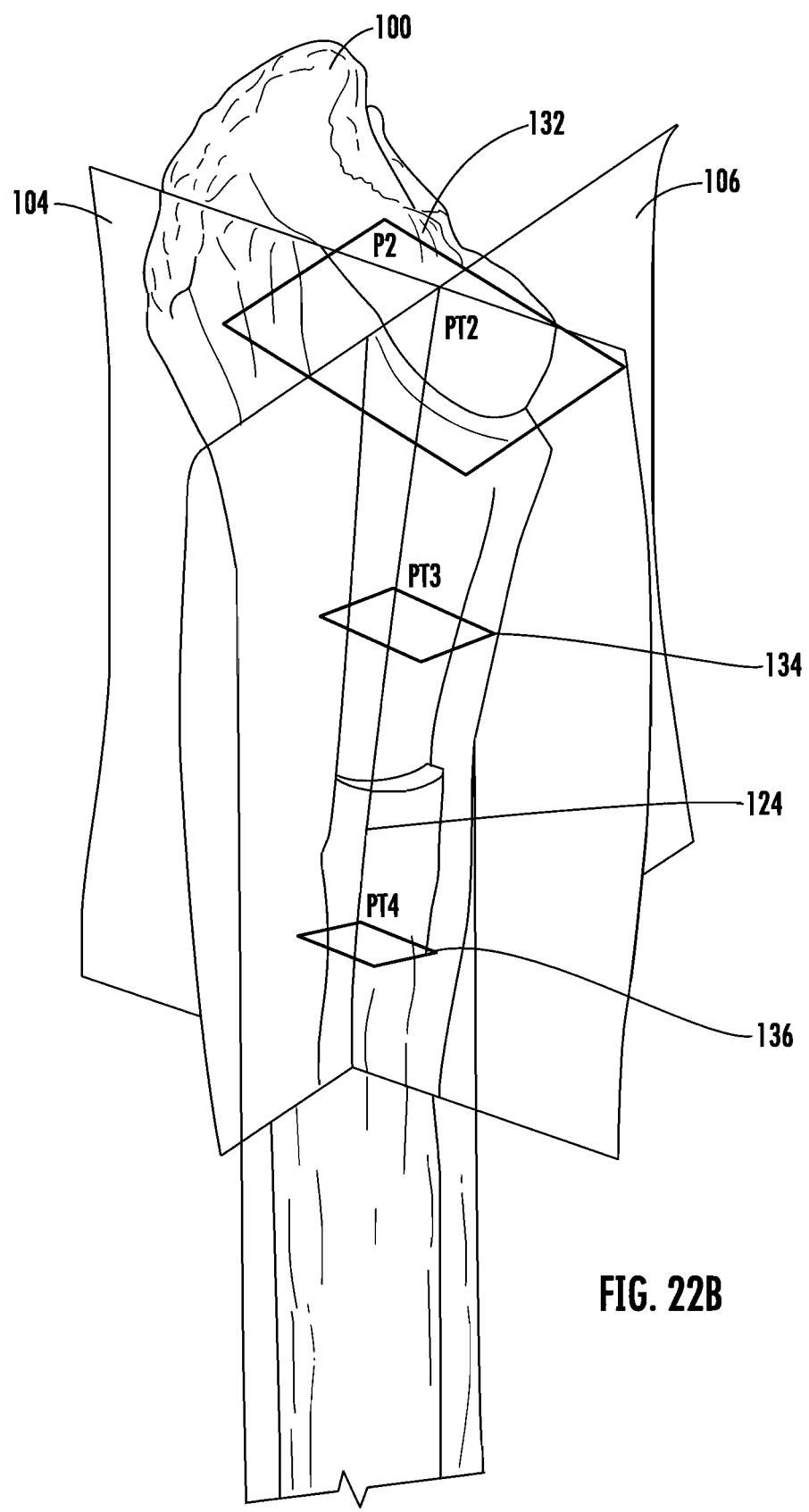
FIG. 22B illustrates the normal cross section planes shown in FIG. 22A, overlaid with the femoral anatomy.
Figure 23A:
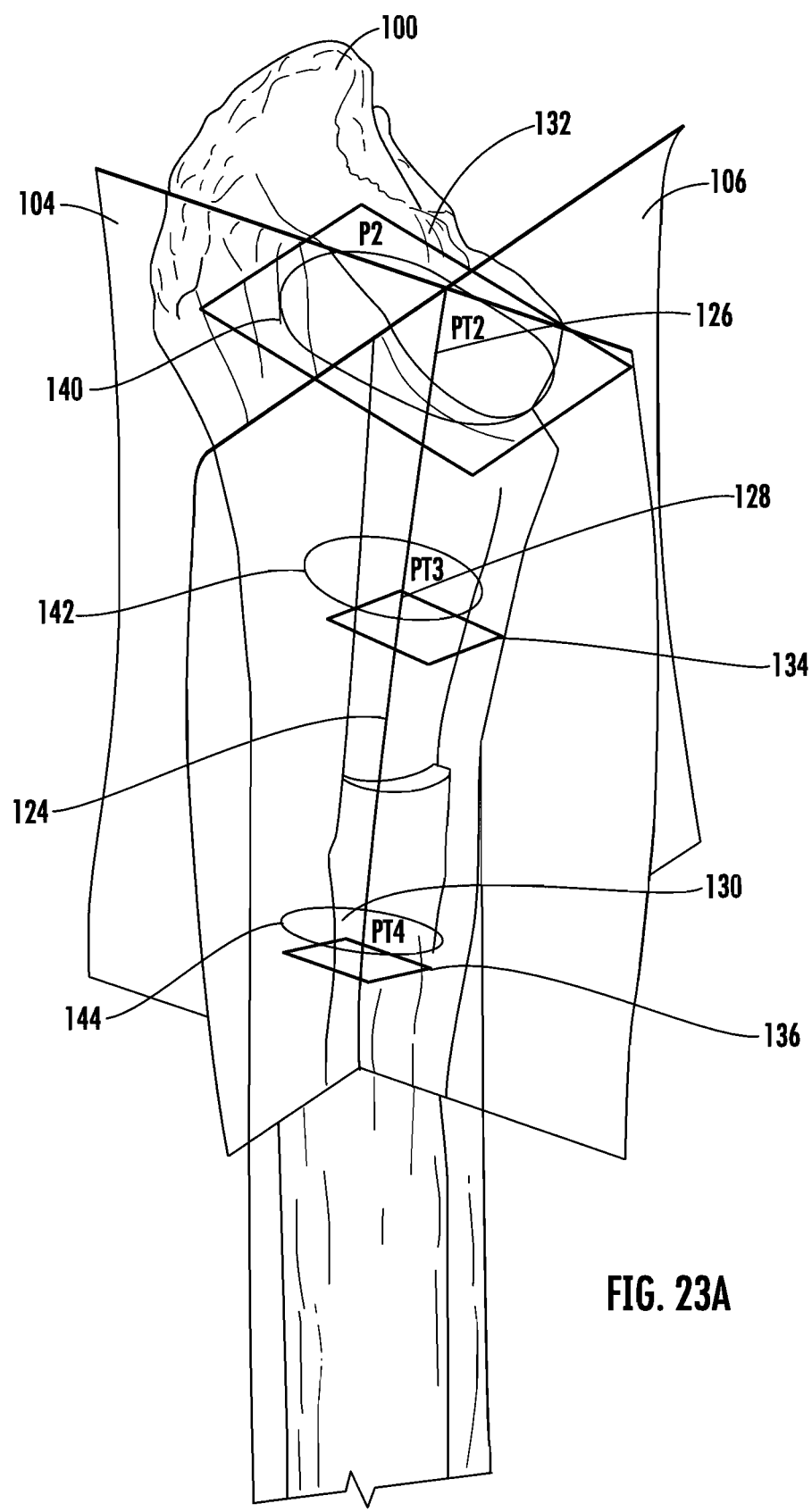
FIG. 23A illustrates the cross sectional geometrical areas on each of the normal planes located by the intermediate reference points on the 3D curve of the hip implant.
Figure 23B:
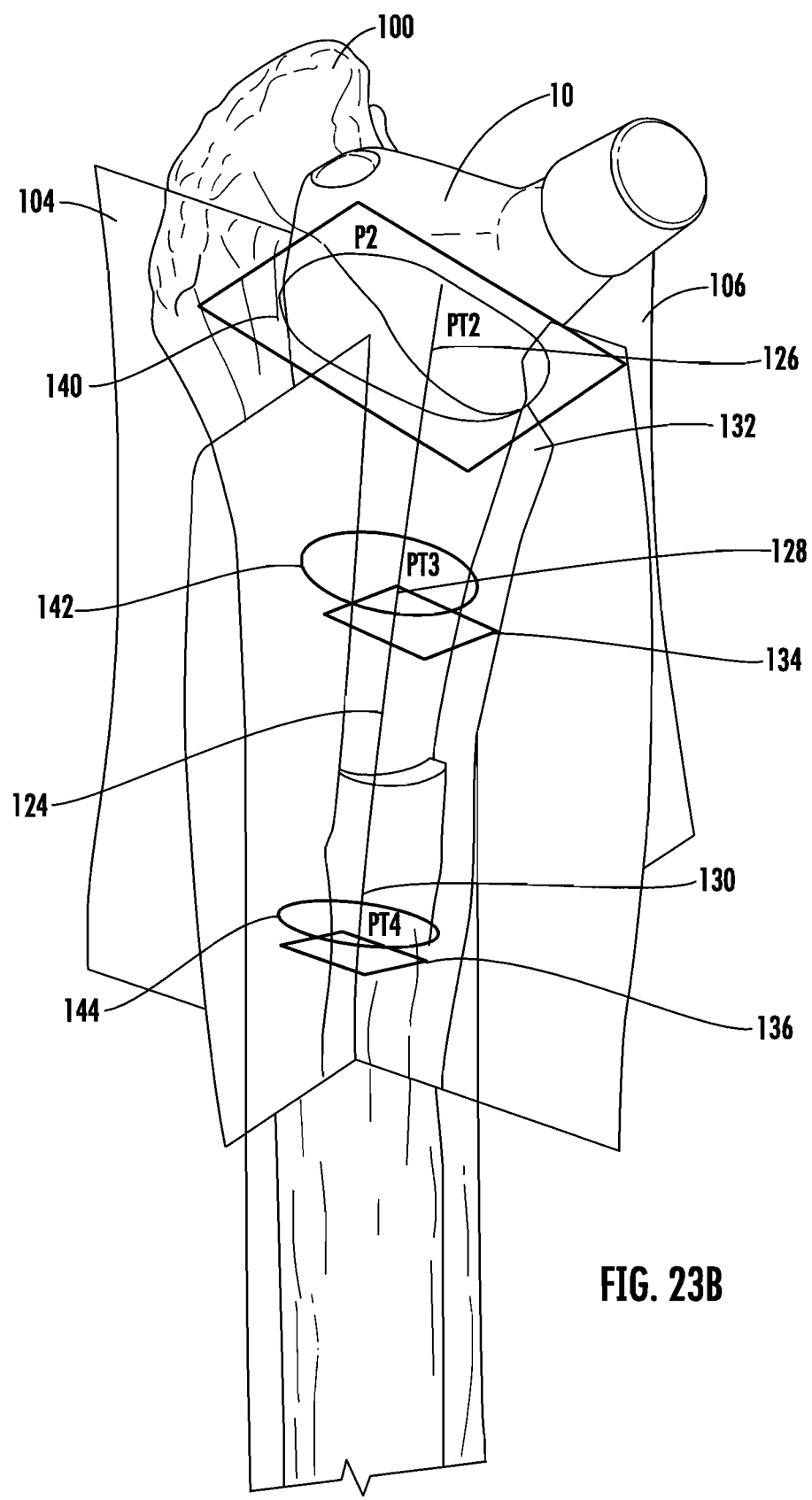
FIG. 23B illustrates the cross sectional geometrical areas shown in FIG. 23A, with the hip implant device inserted into the femur.

A characteristic 3D curve 124 of the hip implant 10 results from projection of the 2D curves (120, 122) created in orthogonal views; see FIGS. 19B and 19D. The characteristic 3D curve 124 can be defined as the intersection of surfaces (AP plane 104, lateral plane 106) created by linearly translating both 2D curves perpendicularly to their respective views, see FIG. 20A and FIG. 20B. Three intermediate reference points, 126 (PT2), 128 (PT3), and 130 (PT4) on the resultant curve 124 are positioned by tabulated parametric arc-length dimensions relative to one end, and selected to produce biaxial alternating 3-point contact of the implant stem in the femoral "cavity"/"socket"/"hole"; see FIG. 21A and FIG. 21B. Cross section planes, 132, 134, and 136, which are normal to the 3D curve 124 are created at each of the three intermediate reference points 126, 128, 130, see FIG. 22A and FIG. 22B. Cross section geometry 140, 142, and 144 can be produced on each cross-section planes 132, 134, 136 with intersecting local surfaces to guide the creation of varying cross sections of the hip implant stem 18, see FIG. 23A. FIG. 23B illustrates the cross-sectional geometry shown in FIG. 23A with the hip implant 10 shown. The hip implant's 10 outer surface may be designed by interpolating modified cross sections along the 3D curve's 124 length.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A hip implant for use in hip replacement surgical procedures comprising:
 a femoral stem body designed for fixation to a femur bone in an anteroposterior (AP) plane and a lateral plane, the femoral stem body extending from a proximal end to a distal tip along a three-dimensional curvature that results from an intersection of a first two-dimensional curvature that follows a first centerline that extends toward the distal tip while remaining equidistant from opposed outer surfaces of the femoral stem body within an anterior-posterior plane, and a second two-dimensional curvature that follows a second centerline that extends toward the distal tip while remaining equidistant from opposed outer surfaces of the femoral stem body within a lateral plane that is orthogonal to said anterior-posterior plane, the femoral stem body including an outer surface having a curvature that corresponds to the three-dimensional curvature,
 wherein said first two-dimensional curvature, said second two-dimensional curvature, or both said first two-dimensional curvature and said second two-dimensional curvature include an inflection point at which the respective curvature changes from concave to convex, and said inflection point is closer to said distal tip than said inflection point is from said proximal end.

2. The hip implant for use in hip replacement surgical procedures according to claim 1, wherein the first two-dimensional curvature and the second two-dimensional curvature are each linearly translated perpendicularly to their respective planes to form the intersection.

3. The hip implant for use in hip replacement surgical procedures according to claim 2, wherein said femoral stem body comprises a longitudinal axis defined by the three-dimensional curvature, and said longitudinal axis extends along a length of said hip implant.

4. The hip implant for use in hip replacement surgical procedures according to claim 3, wherein said femoral stem body defines a cross-sectional shape extending out from said longitudinal axis a sufficient distance so at least a portion of an outer surface of said hip implant is configured to contact an inner surface of a medullary canal.

5. The hip implant for use in hip replacement surgical procedures according to claim 1, wherein said three-dimensional curvature mirrors a curvature of an inner surface of a medullary cavity.

6. The hip implant for use in hip replacement surgical procedures according to claim 5, wherein the femoral stem body includes an outer surface having a curvature that includes an inflection point at which the curvature of the outer surface changes from concave to convex and is configured to cooperate with an inner surface associated with said medullary cavity.

7. The hip implant for use in hip replacement surgical procedures according to claim 1, wherein said femoral stem body has an oval shape in cross section.

8. The hip implant for use in hip replacement surgical procedures according to claim 1, wherein said femoral stem body comprises a neck portion.

9. The hip implant for use in hip replacement surgical procedures according to claim 8, wherein said neck portion terminates in a femoral head engaging member.

10. The hip implant for use in hip replacement surgical procedures according to claim 9, wherein said femoral head engaging member is a locking taper.

11. The hip implant for use in hip replacement surgical procedures according to claim 1, wherein a portion of said femoral stem body includes a porous coating.

12. The hip implant for use in hip replacement surgical procedures according to claim 11, wherein said porous coating includes a titanium plasma spray with a hydroxyapatite coating.

13. The hip implant for use in hip replacement surgical procedures according to claim 1, wherein a cross-sectional shape of said femoral stem body tapers from said proximal end to said distal tip.

14. The hip implant for use in hip replacement surgical procedures according to claim 1, wherein said distal tip has a rounded or blunt shape.

15. The hip implant for use in hip replacement surgical procedures according to claim 14, wherein said distal tip extends from said inflection point to a terminal end of said femoral stem body.

16. The hip implant for use in hip replacement surgical procedures according to claim 15, wherein said distal tip extends along a secondary curvature that is a sufficient length to prevent said distal tip from contacting or running up against any portion of said femur.

17. An implant device for use in surgical procedures, said implant device comprising:
  a femoral stem body designed for fixation in an anterior-posterior plane and a lateral plane that is orthogonal to said anterior-posterior plane, said femoral stem body extending along a longitudinal axis through a proximal end, a distal tip, and a main body that is between said proximal end and said distal tip with respect to said longitudinal axis, the femoral stem body including an outer surface having a curvature that follows the longitudinal axis; and
  a neck portion extending from said proximal end,
  wherein said longitudinal axis follows a three-dimensional curvature formed by an intersection of a two-dimensional curvature that extends toward the distal tip while remaining equidistant from opposed outer surfaces of the main body within said anterior-posterior plane and a two-dimensional curvature that extends toward the distal tip while remaining equidistant from opposed outer surfaces of the main body within said lateral plane, and said two-dimensional curvature formed in said lateral plane includes an inflection point at which the respective curvature changes from concave to convex, and the inflection point is positioned closer to said distal tip than said inflection point is from said neck portion.

18. The implant device of claim 17, further comprising a fastener receiving hole that extends through an opening formed in said proximal end of said femoral stem body, wherein said fastener receiving hole is offset with respect to said longitudinal axis such that said longitudinal axis does not pass through said opening.

19. The implant device of claim 17 wherein said three-dimensional curvature is selected to produce biaxial alternating three-point contact within a femoral cavity in which said implant device is implanted.

20. The implant device of claim 17 wherein said distal tip has a rounded or blunt shape.

21. The implant device of claim 17 wherein the outer surface has a curvature including an inflection point at which the curvature of the outer surface changes from concave to convex.

* * * * *